United States Patent [19]

Baird et al.

[11] Patent Number: 5,464,774
[45] Date of Patent: Nov. 7, 1995

[54] BOVINE BASIC FIBROBLAST GROWTH FACTOR

[75] Inventors: Andrew J. Baird, San Diego; Frederick S. Esch, Foster City; Denis Gospodarowicz, San Francisco, all of Calif.; Peter Bohlen, Cortland, N.Y.; Nicholas C. Ling, San Diego, Calif.

[73] Assignee: The Salk Institute for Biological Studies, San Diego, Calif.

[21] Appl. No.: 139,953

[22] Filed: Dec. 31, 1987

Related U.S. Application Data

[63] Continuation-in-part of Ser. No. 586,518, Mar. 5, 1984, abandoned, Ser. No. 670,160, Nov. 9, 1984, abandoned, Ser. No. 747,154, Jun. 20, 1985, Pat. No. 4,956,455, and Ser. No. 940,524, Dec. 10, 1986, Pat. No. 4,785,079.

[30] Foreign Application Priority Data

Jun. 18, 1986 [WO] WIPO ............... PCT/US86/01318

[51] Int. Cl.⁶ .................................................. C12N 15/18
[52] U.S. Cl. ................................. 536/23.51; 530/399
[58] Field of Search ....................... 435/68, 70, 71, 435/91, 169, 170, 171, 172.1, 172.3, 240.1, 240.2, 320, 849, 940, 253, 254, 255, 256, 257, 258; 536/27, 23.51; 935/9, 10, 11, 22, 23, 24, 27, 28, 29, 33, 34, 38, 59, 60, 61, 66, 68, 69, 70, 71, 72, 73, 74, 75

[56] References Cited

U.S. PATENT DOCUMENTS 4,444,760  4/1984  Thomas, Jr. ............................ 514/21

FOREIGN PATENT DOCUMENTS 8401050  7/1984  WIPO .
8601879  9/1986  WIPO .

OTHER PUBLICATIONS

J. Biol. Chem., 250, 7, 2515–20 (1975), "Purification of Fibroblast Growth Factor," D. Gospodarowicz.
P.N.A.S., 75, 10, 4675–4678 (Oct. 1978), "Brain Derived Fibroblast Growth Factor . . . " Westall et al.
J. Biol. Chem., 255, 12, 5517–5529 (1980), "Brain Fibroblast Growth Factor . . . " Thomas et al.
J. Biol. Chem., 257, 16, 9692–9697 (1982) "Fibroblast Growth Factor from Bovine Pituitary," Gambarini et al.
J. Biol. Chem., 257, 20, 1266–1276 (Oct. 1982), "Purification in High Yield of Brain Fibroblast Growth Factor," D. Gospodarowicz et al.
J. Cell. Biol., 95, 162–169 (Oct. 1982), "Comparison of Brain and Pituitary Preparations," Lemmon et al.
J. Cell. Biochem., 21, 195–208, (1983), "Purification and Partial Characterization . . . " Lemmon et al.
P.N.A.S., 81, 357–361, (Jan. 1984), "Purification and Characterization of Acidic FGF . . . " Thomas et al.
P.N.A.S., 81, 5364–5368, (Sep. 1984), "Isolation and Partial Molecular Characterization of Pituitary FGF", Bohlen et al.
P.N.A.S., 81, 6963–6967, (Nov. 1984), "Isolation of Brain FGF by Heparin–Sepharose . . . ", Gospodarowicz et al.
J. of Cell. Biochem., 29, Supple. 9A, 1985, "Molecular Characterization of Bovine and Human FGF", Bohlen et al.
J. Cell. Physiol., 122, 323–332, (1985), "Isolation of Pituitary Fibroblast Growth Factor . . . ", D. Gospodarowicz et al.
Maniatis et. al. (1982). "Molecular Cloning: A Laboratory Manual", Cold Spring Harbor Laboratory, N.Y. 545 pages.

Primary Examiner—Richard A. Schwartz
Assistant Examiner—Douglas Gurian-Sherman
Attorney, Agent, or Firm—Fitch, Even, Tabin & Flannery

[57] ABSTRACT

Substantially pure mammalian basic fibroblast growth factors are produced. The amino acid residue sequences of bovine and human bFGF are disclosed as well as a DNA chain encoding the polypeptide of the bovine species. By appropriately inserting a synthesized DNA chain into a cloning vector and using the cloning vector to transform cells, synthetic bovin bFGF can be obtained from transformed cell lines, both prokaryotic and eukaryotic.

3 Claims, No Drawings

BOVINE BASIC FIBROBLAST GROWTH FACTOR

This invention was made with Government support under Grants HD-09690, AM-18811, HL-20197 and EY-02186 awarded by the National Institutes of Health (DHHS). The Government has certain rights in this invention. This application is a continuation-in-part of U.S. applications Ser. No. 586,518 filed Mar. 5, 1984, (abandoned), Ser. No. 670,160 filed Nov. 9, 1984, (abandoned), Ser. No. 747,154 filed Jun. 20, 1985, now U.S. Pat. No. 4,956,455, and Ser. No. 940,524, filed Dec. 10, 1986, now U.S. Pat. No. 4,785,079. The present invention is directed to basic fibroblast growth factor (FGF) produced by synthetic methods, which will substantially enhance the availability of mammalian basic FGF.

BACKGROUND OF THE INVENTION

Both the brain and the pituitary gland have been known to contain mitogenic factors for cultured cells; however, until 1974, it was unclear what their relationship was with classical pituitary hormones, such as TSH, LH, FSH, GH and ACTH. In 1974, the identification in the pituitary gland of a growth factor called fibroblast growth factor (FGF) was reported which was shown to be distinct from pituitary hormones, Gospodarowicz, D., Nature, 249: 123–127 (1974). This growth factor is now known to have a MW of 16,415, is basic (a pI of 9.6), and is a potent mitogen for either normal diploid fibroblasts or established cell lines. It is thus referred to as "basic FGF" because it exhibits such a basic pI of 9.6 (in contrast to acidic FGF which has an acidic pI of about 5). Purification of an acidic brain FGF is described in U.S. Pat. No. 4,444,760 (Apr. 24, 1984). To distinguish from the acidic FGF, the compounds of present interest are referred to as basic FGF. Later studies confirmed that, in addition to fibroblasts, FGF is also mitogenic for a wide variety of normal diploid mesoderm-derived and neural crest-derived cells, including granulocytes, adrenal cortical cells, chondrocytes, myoblasts, corneal and vascular endothelial cells from either bovine or human origin, vascular smooth muscle cells, and lens epithelial cells. Basic FGF was also shown to substitute for platelet-derived growth factor in its ability to support the proliferation of fibroblasts exposed to plasma-supplemented medium. Consistent with its ability to stimulate the proliferation of bovine vascular endothelial cells, basic FGF has a similar activity in vivo on capillary endothelial cells; therefore, basic FGF is considered an angiogenic factor.

The first above-identified U.S. application, Ser. No. 586,518, the teachings of which are incorporated herein by reference, describes a purification to homogeneity of mammalian basic fibroblast growth factor (FGF) using reverse-phase high performance liquid chromatography (RP-HPLC). The second above-identified U.S. application, Ser. No. 670,160, the teachings of which are incorporated herein by reference, describes a purification to homogeneity of mammalian FGF using heparin-Sepharose affinity chromatography which has certain advantages.

SUMMARY OF THE INVENTION

As described in application Serial No. 586,518, starting with a preparation of partially purified basic fibroblast growth factor of pituitary origin (Gospodarowicz et al., J. Biol. Chem. 250: 2515, 1975), purification to substantial homogeneity is effected by cation exchange HPLC and two reverse-phase HPLC steps to produce basic FGF having mitogenic properties. Relatively low hydrophobicity stationary phases, such as C3 to C8 silica gel columns, using at least two different mobile phases, were found to provide good recovery and high resolution of FGF regardless of the sequence in which they were used. Isolation is monitored by testing column fractions for their ability to stimulate proliferation of cultured bovine aortic endothelial cells. Amino acid composition and N-terminal amino acid sequence of the protein (MW 15,800 by polyacrylamide gel electrophoresis) indicated that its structure was different from that of other known growth factors, including brain acidic FGF. The HPLC purified protein exhibited high activity in vitro in stimulating division ($ED_{50}$ 0.25 ng/ml) of vascular (aortic and umbilical vein) endothelial cells, vascular smooth muscle cells, adrenal cortical cells, chondrocytes and granulosa cells, but not basal epithelial cells.

Continuing work shows that the above-mentioned partially purified basic FGF can alternatively be subjected to cation exchange chromatography on a Mono S column using a Gilson HPLC system, following chromatography on a Sephadex G-75 column. By using such a Mono S column twice with a different mobile phase system each time, homogeneity of the basic FGF is obtained, the details of the process being described in J. Cell. Phis. 122: 323–332 (1985). It was found that concentrations of basic FGF which has been purified in this manner as low as 20 picomolar stimulated cell product proliferation maximally, and that half-maximal response ($ED_{50}$) was observed at 1.5–3 pM.

As described in U.S. applications Ser. No. 670,160, filed Nov. 9, 1984 and Ser. No. 940,824, filed Dec. 10, 1986, basic brain and pituitary fibroblast growth factors can each be purified to apparent homogeneity from crude tissue extracts by a simplified method which includes a rough pre-purification protocol followed by affinity chromatography procedure using a column in which heparin is linked to an insoluble support. Heparin is a highly sulfated dextrorotary mucopolysaccharide which is a constituent of several mammalian tissues, especially the liver and lungs, the chief clinical utility of which is as an anticoagulant. It was surprising that, from relative crude preparations of both brain and pituitary tissue, basic fibroblast growth factor is adsorbed by heparin in the affinity chromatography to the virtual exclusion of other brain and pituitary proteins.

Pure mammalian basic FGF, such as bovine pituitary basic fibroblast growth factor may now be synthesized using recombinant DNA techniques or other suitable techniques. Bovine basic FGF is a 146 amino acid residue polypeptide having the sequence set forth hereinafter. Other mammals appear to have homologous or equivalent bFGF molecules. It appears most likely that, in the native molecule, none of the four cysteine residues are disulfide bonded to each other, but that there may be bonding of one or more of the cysteine residues to free cysteine molecules. However, evidence for there being no internal disulfide-bonding between cysteine residues is not fully conclusive, and one or two pairs of cysteine residues may be internally bonded to each other. If there is such internal bonding of cysteine residues, it is not certain which pair or pairs of cysteine residues are involved. In any case, the present invention provides biologically active peptides, whether non-bonded or randomly bonded. Because bFGF is a relatively long-chain peptide, synthesis by a recombinant DNA technique is presently a synthetic method of choice, as opposed to standard chain elongation procedures involving stepwise addition of amino acid residues. Extraction and purification are possible but are not considered to be commercially feasible at the present time.

Accordingly, a bFGF-encoding DNA chain is obtained using a method known to those skilled in this art, e.g., by oligonucleotide synthesis or by cloning cDNA which one obtains, via the use of reverse transcriptase, from the RNA isolated from cells known to produce bFGF, and the synthetic DNA chain is inserted into a cloning vector, appropriately placed therein so as to ensure its expression when the recombinant cloning vector is introduced into an organism or cell line. Synthetic bFGF polypeptides which either have no internal disulfide bonds or which are randomly disulfide bonded exhibit biological activity.

Pharmaceutical compositions in accordance with invention include bFGF, a bFGF analog, biologically active fragments of bFGF or of analog bFGF, or nontoxic salts thereof dispersed in a pharmaceutically acceptable liquid or solid carrier. Such pharmaceutical compositions can be used in clinical medicine, both human and veterinary, in acute or chronic administration for diagnostic or therapeutic purposes. bFGF is further useful in in-vitro cell proliferation procedures. Also considered to be within the scope of the invention are biologically active fragments of the full length bFGFs or polypeptides with additional segments added to either or both termini, such as those which arise from considerations of vector construction when the peptides are made using recombinant DNA techniques, providing that such terminal segments do not destroy the biological activity of the peptide.

DETAILED DESCRIPTION OF CERTAIN PREFERRED EMBODIMENTS

The invention provides the first known pure mammalian basic FGF, so-called bFGF, and the production thereof by synthetic methods. The nomenclature used to define the peptides is that specified by Schroder & Lubke, "The Peptides", Academic Press (1965), wherein in accordance with conventional representation the residue having the free alpha-amino group at the N-terminus appears to left and the residue having the alpha-carboxyl group at the C-terminus to the right. Where the amino acid residue has isomeric forms, it is the L-form of the amino acid that is represented.

The molecular weight of an exemplary pure protein from the separation procedure using cation-exchange HPLC on bovine tissue and two reverse-phase HPLC steps was determined to be about 15,800. Table I shows the amino acid composition of the bovine mitogen. The analysis shown is based on the above molecular weight and indicates that the protein contains about 140 amino acid residues and may be a polypeptide containing about 137 amino acids residues. Moreover, the compositions obtained from 4 different batches agree well, which is further evidence of the high purity of the protein.

TABLE I

AMINO ACID COMPOSITION OF GROWTH FACTOR (FGF)
(Four Different Preparations)

| | Batch Number | | | | | |
|---|---|---|---|---|---|---|
| | 1 | 2 | 3 | 4 | average | integer |
| Asx | 11.06 | 11.35 | 11.75 | 10.78 | 11.24 ± 0.42 | (11) |
| Thr | 3.83 | 3.78 | 3.39 | 3.27 | 3.6 ± 10.26 | (4) |
| Ser | 8.92 | 9.02 | 8.06 | 7.97 | 8.4 ± 80.56 | (13) |
| Glx | 13.36 | 12.88 | 12.75 | 12.37 | 12.8 ± 40.40 | (13) |
| Pro | 7.97 | 8.46 | n.d. | 9.12 | 8.4 ± 90.61 | (8) |
| Gly | 15.26 | 15.82 | 14.06 | 15.11 | 15.0 ± 60.55 | (16) |

TABLE I-continued

AMINO ACID COMPOSITION OF GROWTH FACTOR (FGF)
(Four Different Preparations)

| | Batch Number | | | | | |
|---|---|---|---|---|---|---|
| | 1 | 2 | 3 | 4 | average | integer |
| Ala | 9.03 | 8.34 | 8.68 | 8.06 | 8.5 ± 60.42 | (9) |
| Cys | 5.59 | 5.47 | n.d. | 5.19 | 5.4 ± 20.20 | (5) |
| Val | 4.77 | 5.68 | 5.04 | 6.28 | 5.4 ± 20.67 | (5) |
| Met | 1.29 | 1.61 | 1.96 | 1.13 | 1.5 ± 10.37 | (2) |
| Ile | 2.82 | 2.45 | 3.58 | 3.47 | 3.0 ± 90.54 | (3) |
| Leu | 12.34 | 11.77 | 12.66 | 11.86 | 2.2 ± 00.42 | (12) |
| Tyr | 6.14 | 6.47 | 5.75 | 6.61 | 6.2 ± 60.38 | (6) |
| Phe | 6.76 | 7.00 | 6.53 | 6.68 | 6.8 ± 20.20 | (7) |
| His | 1.64 | 1.64 | 2.74 | 2.68 | 2.1 ± 80.62 | (2) |
| Trp | 0.19 | 0.49 | 0.54 | n.d. | 0.4 ± 00.19 | (1) |
| Lys | 12.13 | 11.86 | 13.18 | 13.27 | 12.6 ± 50.72 | (13) |
| Arg | 10.96 | 10.60 | 10.28 | 10.54 | 10.6 ± 20.28 | (11) |

Values represent residues/molecules determined from 24 h hydrolysates of 5–10 pmol protein and are not corrected for hydrolysis losses.
n.d. - not determined.

By sequencing the purified peptide, the following amino terminal sequence was established:

Pro-Ala-Leu-Pro-Glu-Asp-Gly-Ser. Antibodies were then raised in rabbits against a synthetic decapeptide representing the amino terminal sequence of the pituitary-derived growth factor. The antisera recognize the synthetic peptide and the growth factor on an equimolar basis and are capable of inhibiting the mitogenic activity of the native protein in vitro. Amino terminal-directed antibodies to pituitary FGF were obtained by immunizing three month old male and female white New Zealand rabbits with the synthetic decapeptide H-Pro-Ala-Leu-Pro-Glu-Asp-Gly-Gly-Ser-Tyr-OH. The antigen was coupled to bovine serum albumin (BSA) by a bis-diazotized benzidine(BDB) linkage. Coupling time was 2 h at 4° C. The reaction mixture was dialized to remove low molecular weight material, and the retentate was frozen in 2 ml aliquots in liquid nitrogen and stored at −20° C. Animals were immunized with the equivalent of 1 mg of the peptide antigen according to the procedure of Benoit et al. P.N.A.S USA, 79, 917–921 (1982). At three week intervals, the animals were boosted by injections of 200 ug of the antigen peptide and bled ten to fourteen days later. After the third boost, antiserum was examined for its capacity to bind radioiodinated antigen peptide prepared by the chloramine-T method and purified by DEAE-ion exchange column chromatography using 0.6N ammonium acetate pH=8.5 for elution of the iodinated antigen peptide.

A radioimmunoassay was established with the antisera RB715B3, RB716B3, and serum from subsequent bleeds from the same rabbits. The native protein mitogen is recognized by the antibodies on an equimolar basis as compared to the synthetic peptide antigen. The sensitivity of the RIA enables the detection of 500 pg (about 30 fmol) of growth factor. Preliminary data indicate that immunoreactive protein can be located in commercial sources of FGF from Collaborative Research, in standard ovine luteinizing hormone preparations of bovine and human brain, in extracts of human placenta, rat pituitary and rat atria. The material is not ubiquitous, however, since it cannot be detected in extracts of bovine adrenal medualla, cortex or pituitary intermediate lobe.

In preliminary experiments, it was shown that the antibodies are capable of partially neutralizing the biological activity of the growth factor on bovine aortic endothelial cells in-vitro. It was found likely that substantially all activity can be neutralized when higher amounts of antibodies are used.

Using the RIA, an attempt was also made to quantify the growth factor in bovine pituitary tissue. While with the isolation of only 5 nmol/Kg was obtained, immunological data (obtained with crude extracts) suggest the presence of much larger quantities (approximately 70 nmol/kg); levels which are quite comparable to those of other pituitary hormones. It was believed that immunoaffinity chromatography could be applied to achieve the large scale purification of the growth factor.

Using the RIA, it was demonstrated that bovine anterior pituitary cells in monolayer culture release the mitogenic protein into the culture medium. This release is stimulated by short term incubation (4 h) of pituitary cells with depolarizing agents, such as 50 mM KCl (3-fold stimulation over control), or by activation of the adenylate cyclase system with $10^4$M forskolin (3-fold stimulation). These data suggested that the growth factor is actively secreted from the pituitary.

Exposure of partially purified FGF to acid conditions results in drastic loss of bioactivity. When partially purified FGF, i.e., fractions from Mono S column, was subjected to reverse phase HPLC (pH 2 on C3 column) or even organic solvents at neutral pH, 90–95% of the bioactivity was lost without a concommitant loss of protein mass, which results in a yield of only about 5 nmol/kg of pituitaries.

Subsequent purification of larger quantities of mammalian bFGF from bovine pituitaries allowed the entire sequence to be analyzed, and thus the invention provides peptides having, for example, the formula:

of this application, mammalian bFGF peptides should be considered to constitute peptides having the 146 amino-acid-residue sequence as well as naturally occurring mammalian amino acid sequence variants thereof and biologically active fragments of the foregoing. The bFGFs isolated from various tissues exhibit significant microheterogeneity, particularly at the N-terminus (e.g., bFGF (12–146) in liver and bFGF (16–146) in kidney, adrenal glands and testes) (see, Ueno, N. et al., *Biochem. and Biophys. Res. Comm.* 138:580–588 (1986), which is incorporated herein by reference).

It will also be readily apparent to those skilled in the art that various bFGF fragments, e.g.,., bFGF (24–120)-OH and bFGF (30–110)-NH$_2$, may be utilized to mimic one or more activities of the naturally-occurring forms of the protein. Biologically active fragments can act as agonists or antagonists. Small fragments (e.g., bFGF (24–68) and bFGF (106–120) have essentially the same intrinsic activity, but lower potency than the longer naturally-occurring bFGFs (see, Schubert, D. et al., *J. Cell Biol.* 104:635–643 (1987), which is incorporated herein by reference).

From presently available evidence, it is most likely that there is no internal disulfide-bonding between cysteine residues of the chain. However, two of the cysteine residues may be internally disulfide-bonded to each other, and the residues at positions 25 and 69 are likely candidates for such internal bonding. Although it appears unlikely, disulfide bonding may also occur between two pairs of the cysteine residues. Also, one or more of the cysteine residues, excluding any which are involved in internal disulfide bonding, may be bonded to free cysteine. The invention is intended to encompass synthetically produced bFGF polypeptides in which the

```
  1    2    3    4    5    6    7    8    9   10   11   12   13
H—Pro—Ala—Leu—Pro—Glu—Asp—Gly—Gly—Ser—Gly—Ala—Phe—Pro—

14   15   16   17   18   19   20   21   22   23   24   25   26
Pro—Gly—His—Phe—Lys—Asp—Pro—Lys—Arg—Leu—Tyr—Cys—Lys—

27   28   29   30   31   32   33   34   35   36   37   38   39
Asn—Gly—Gly—Phe—Phe—Leu—Arg—Ile—His—Pro—Asp—Gly—Arg—

40   41   42   43   44   45   46   47   48   49   50   51   52
Val—Asp—Gly—Val—Arg—Glu—Lys—Ser—Asp—Pro—His—Ile—Lys—

53   54   55   56   57   58   59   60   61   62   63   64   65
Leu—Gln—Leu—Gln—Ala—Glu—Glu—Arg—Gly—Val—Val—Ser—Ile—

66   67   68   69   70   71   72   73   74   75   76   77   78
Lys—Gly—Val—Cys—Ala—Asn—Arg—Tyr—Leu—Ala—Met—Lys—Glu—

79   80   81   82   83   84   85   86   87   88   89   90   91
Asp—Gly—Arg—Leu—Leu—Ala—Ser—Lys—Cys—Val—Thr—Asp—Glu—

92   93   94   95   96   97   98   99  100  101  102  103  104
Cys—Phe—Phe—Phe—Glu—Arg—Leu—Glu—Ser—Asn—Asn—Tyr—Asn—

105  106  107  108  109  110  111  112  113  114  115  116  117
Thr—Tyr—Arg—Ser—Arg—Lys—Tyr—Ser—Ser—Trp—Tyr—Val—Ala—

118  119  120  121  122  123  124  125  126  127  128  129  130
Leu—Lys—Arg—Thr—Gly—Gln—Tyr—Lys—Leu—Gly—Pro—Lys—Thr—

131  132  133  134  135  136  137  138  139  140  141  142  143
Gly—Pro—Gly—Gln—Lys—Ala—Ile—Leu—Phe—Leu—Pro—Met—Ser—

144  145  146
Ala—Lys—Ser—Y,
``` wherein Y is OH or NH$_2$. It is uncertain whether the C-terminus of the native molecule is amidated. For purposes cysteines are free or have random internal disulfide bonds randomly, i.e., between positions 25 and 69; 25 and 87; 25 and 92; 69 and 87; 69 and 92; 87 and 92; 25 and 69 plus 87 and 92; 25 and 87 plus 69 and 92; and 25 and 92 plus 69 and 87. A mixture of FGF peptides in which cysteine residues are non-bonded or randomly bonded exhibits at least some biological activity.

In any event, mammalian bFGF polypeptides produced by recombinant DNA techniques are inherently biologically active. This may be because the three-dimensional structure which the bFGF assumes within cells is the structure recognized by the receptor. The three-dimensional structure which the molecule assumes through natural folding and through hydrophobic and hydrophilic interactions with aqueous media may promote desired bonding or non-bonding between cysteine residues. Also, enzymatic regulatory mechanisms within cells may help to ensure desired disulfide bonding or non-bonding, either by preventing bonding or by directing disulfide bonding between particular cysteine residues. Enzymes might also cleave "incorrect" bonding to enable the molecule to reorient itself and assume the correct natural structure. Cysteine residues that are not internally bonded may be disulfide-bonded to free cysteine moieties. It may also be that the three-dimensional structure of the molecule is such that random bonding or non-bonding of cysteine residues either with each other to free cysteines does not substantially affect the biological structure of the protein molecule.

To synthesize a protein having the mammalian bFGF amino acid residue sequence by recombinant DNA, a double-stranded DNA chain which encodes bFGF is synthetically constructed. The segment of the DNA chain that encodes bFGF is, of course, designed according to the genetic code; however, because of the degeneracy of the genetic code, a wide variety of codon combinations can be selected to form the DNA chain that encodes the product polypeptide. It is known that certain codons are more efficient for polypeptide expression in certain types of organisms, and the selection of codons preferably is made according to those codons which are most efficient for expression in the type of organism which is to serve as the host for the recombinant vector. However, any correct set of codons will encode product, even if slightly less efficiently. Codon selection may also depend upon vector construction considerations; for example, it may be necessary to avoid placing a restriction site in the DNA chain if, subsequent to inserting the synthetic DNA chain, the vector is to be manipulated using the restriction enzyme that cleaves at such a site. Also, it is necessary to avoid placing restriction sites in the DNA chain if the host organism which is to be transformed with the recombinant vector containing the DNA chain is known to produce a restriction enzyme that would cleave within the DNA chain.

In addition to the bFGF-encoding sequences, the DNA chain that is synthesized may contain additional sequences, depending upon vector construction considerations. Typically, the DNA chain is synthesized with linkers at its ends to facilitate insertion into restriction sites within a cloning vector. The DNA chain may be constructed so as to encode the bFGF amino acid sequences as a portion of a fusion polypeptide; and if so, it will generally contain terminal sequences that encode amino acid residue sequences that serve as proteolytic processing sites, whereby the bFGF polypeptide may be proteolytically cleaved from the remainder of the fusion polypeptide. The terminal portions of the synthetic DNA chain may also contain appropriate start and stop signals.

To assemble a bFGF-encoding DNA chain, oligonucleotides are constructed by conventional methods, such as procedures described in T. Manatis et al., *Cold Spring Harbor Laboratory Manual*, Cold Spring Harbor, N.Y. (1982) (hereinafter, CSH). Sense and antisense oligonucleotide chains, up to about 70 nucleotide residues long, are synthesized, preferably on automated synthesizers, such as the Applied Biosystem Inc. model 380A DNA synthesizer. The oligonucleotide chains are constructed so that portions of the sense and antisense oligonucleotides overlap, associating with each other through hydrogen binding between complementary base pairs and thereby forming double stranded chains, in most cases with gaps in the strands. Subsequently, the gaps in the strands are filled in and oligonucleotides of each strand are joined end to end with nucleotide triphosphates in the presence of appropriate DNA polymerases and/or with ligases.

As an alternative to construction of a synthetic DNA chain through oligonucleotide synthesis, cDNA corresponding to bFGF may be prepared. A cDNA library or an expression library is produced in a conventional manner by reverse transcription from messenger RNA (mRNA) from a bFGF-producing mammalian cell line. To select clones containing bFGF sequences, hybridization probes (preferably mixed probes to accommodate the degeneracy of the genetic code) corresponding to portions of the bFGF protein are produced and used to identify clones containing such sequences. Screening of he expression library with bFGF antibodies may also be used, alone or in conjunction with hybridization probing, to identify or confirm the presence of bpFGF-encoding DNA sequences in DNA library clones. Such techniques are taught, for example in CSH, supra.

The double-stranded bFGF-encoding DNA chain is constructed or modified with insertion into a particular appropriate cloning vector in mind. The cloning vector that is to be recombined to incorporate the DNA chain is selected appropriate to its viability and expression in a host organism or cell line, and the manner of insertion of the DNA chain depends upon factors particular to the host. For example, if the DNA chain is to be inserted into a vector for insertion into a prokaryotic cell, such as *E. coli*, the DNA chain will be inserted 3' of a promoter sequence, a Shine-Delgarno sequence (or ribosome binding site) that is within a 5' non-translated portion and an ATG start codon. The ATG start codon is appropriately spaced from the Shine-Delgarno sequence, and the coding sequence is placed in correct reading frame with the ATG start codon. The cloning vector also provides a 3' non-translated region and a translation termination site. For insertion into a eukaryotic cell, such as a yeast cell or a cell line obtained from a higher animal, the bFGF-encoding oligonucleotide sequence is appropriately spaced from a capping site and in correct reading frame with an ATG start signal. The cloning vector also provides a 3' non-translated region and a translation termination site.

Prokaryotic transformation vectors, such as pBR322, pMB9, Col E1, pCR1, RP4 and lambda-phage, are available for inserting a DNA chain of the length which encodes bFGF with substantial assurance of at least some expression of the encoded polypeptide. Typically, such vectors are constructed or modified to have a unique restriction site(s) appropriately positioned relative to promoter, such as the lac promoter. The DNA chain may be inserted with appropriate linkers into such a restriction site, with substantial assurance of production of bFGF in a prokaryotic cell line transformed with the recombinant vector. To assure proper reading frame, linkers of various lengths may be provided at the ends of the bFGF-encoding sequences. Alternatively, cassettes, which include sequences, such as the 5' region of the lac Z gene (including the operator, promoter, transcription start site, Shine Delgarno sequence and translation initiation signal), the regulatory region from the tryptophane gene (trp operator, promoter, ribosome binding site and translation initiator), and a fusion gene containing these two promoters called the trp-lac (Tac) promoter are available into which the synthetic DNA chain may be conveniently inserted and then the cassette inserted into a cloning vector of choice.

Similarly, eukaryotic transformation vectors, such as the cloned bovine papilloma virus genome, the cloned genomes of the murine retroviruses, and eukaryotic cassettes, such as the pSV-2 gpt system (described by Mulligan and Berg, *Nature* 277, 108–114, 1979) the Okayama-Berg cloning system (*Mol. Cell Biol.*, 2: 161–170, 1982), the expression cloning vector recently described by Genetics Institute (*Science* 228: 810–815, 1985), are available which provide substantial assurance of at least some expression of bFGF in the transformed eukaryotic cell line.

A convenient way to ensure production of bFGF or a polypeptide of a similar length is to produce the polypeptide initially as a segment of a gene-encoded fusion polypeptide. In such case, the DNA chain is constructed so that the expressed polypeptide has enzymatic processing sites flanking the bpFGF amino acid residue sequences. A bFGF-encoding DNA chain may be inserted, for example, into the beta-galactosidase gene for insertion into *E. coli*, in which case, the expressed fusion polypeptide is subsequently cleaved with proteolytic enzymes to release the bFGF from beta-galactosidase peptide sequences.

An advantage of inserting the bFGF-encoding sequence so that the bFGF sequence is expressed as a cleavable segment of a fusion polypeptide, e.g., as the bFGF peptide sequence fused within the beta-galactosidase peptide sequence, is that the endogenous polypeptide into which the bFGF sequence is inserted is generally rendered non-functional, thereby facilitating selection for vectors encoding the fusion peptide.

EXAMPLE 1

The complete structure of bovine bFGF was determined as follows:

Frozen bovine pituitaries were homogenized with a Waring blender for 5 minutes in 0.15M ammonium sulfate (4 liter/kg tissue). The pH was then adjusted to 4.5 with HCl and the homogenate stirred vigorously for 2 hours. After centrifugation (18,000×g, 30 minutes) the supernatant was retained, and 230 g ammonium sulfate per liter of supernatant were added; the pH was adjusted to 6–6.5 with NaOH; and the precipitation was allowed to proceed for 15 hours. After centrifugation of the reaction mixture (18,000×g, 30 min), the supernatant was retained; 300 g ammonium sulfate were added to each liter of the supernatant; and then the mixture stirred well for two hours. After centrifugation of the reaction mixture (18,000×g, 30 min), the pellet was retained, and the cumulative pellets from 3 kg starting tissue was dissolved in 200 ml distilled water and dialyzed against 20 liters of distilled water overnight. The pH of the dialyzed retentate was then adjusted to 6, and the solution was clarified by centrifugation (12,000×g, 30 min). The dialyzed retentate constitutes a dialyzed extract.

Basic FGF was subsequently isolated from the dialyzed, clarified extract using three successive protocols; two of these employed conventional ion-exchange and reverse phase HPLC purification steps as described previously (P. Bohlen et al. *Proc. Natl. Acad. Sci. USA* 81: 5364–5368 (1984)). The third method utilized heparin-Sepharose affinity chromatography in a key purification step as detailed as follows in the order in which they were performed.

(A) CM-Sephadex (C50) ion-exchange chromatography

A 7×9 cm column of carboxymethyl Sephadex (C50) was washed with 1 liter of 50 mM sodium phosphate, 1.5M sodium chloride, pH 6.0 and then equilibrated with 0.1M sodium phosphate, pH 6.0. The dialyzed extract from 3 kg bovine pituitaries was loaded onto the column, and the column was washed sequentially with 0.1M sodium phosphate, pH 6.0 containing a) no NaCl, b) 0.2M NaCl and c) 0.65M NaCl, allowing the $OD_{280}$ to reach a minimum value before initiating each new wash. Fractions of 18 ml were collected at 3 ml/min at 4° C. and subjected to radioimmunoassay.

(B) Heparin-Sepharose chromatography.

The 0.65M NaCl eluate from CM-Sephadex chromatography was loaded onto a 3×3 cm column of heparin-Sepharose (Pharmacia) previously equilibrated with 10 mM Tris-HCl, 0.6M NaCl, pH 7.0 at room temperature. The column was then washed sequentially with 10 mM Tris-HCl, pH 7.0 containing a) 0.6M NaCl and b) 1.1M NaCl, allowing the $OD_{280}$ to reach a minimum value with each wash. The basic FGF was then eluted with a linear gradient in 10 mM Tris-HCl, pH 7.0 containing 100 ml 1.1M NaCl and 100 ml 2M NaCl. Fractions of 5 ml were collected at 0.8 ml/min and subjected to radioimmunoassay.

(C) Reverse phase liquid chromatography.

The basic FGF from heparin-Sepharose chromatography was pumped onto a Vydac C-4 (0.46×25 cm) reverse phase column (The Separations Group, Inc.) using a 0.1% trifluoroacetic acid (TFA)/acetonitrile solvent system (F. S. Esch et al. *Methods in Enzymol.* (ed. Conn, P.) 103, Academic Press, New York, pp. 72–89 (1983)) and eluted at 0.6 ml/min. with a 90 min. gradient of 23% to 35% acetonitrile. Fractions of 3 ml were collected at room temperature and subjected to radioimmunoassay.

In the above mentioned Radioimmunoassays (RIA) for basic FGF, antibodies were generated against a synthetic analog of the amino terminal sequence of basic FGF, [$Tyr^{10}$] bFGF(1–10) which is conjugated to bovine serum albumin, and were subsequently used to develop the radioimmunoassay for basic FGF, as described in A. Baird et al. *Regulatory Peptides* 10, 309–317 (1985).

Because it is not possible to quantitate unmodified cysteine by amino acid analysis, cysteine residues were modified either by reduction and alkylation with [$^{14}C$]iodoacetamide (New England Nuclear) or oxidization with performic acid as indicated below. In either case, the bFGF in 0.1% TFA/acetonitrile was dried in a 1.5 ml polypropylene microfuge tube in a Speed Vac vacuum centrifuge (Savant, Inc.) just prior to modification.

The reduction and alkylation of cysteine residues was performed in order to radioactively label cysteine residues, making it possible to determine which fragments of subsequent cleavage reactions contain cysteine residues. The dried bFGF was dissolved in 0.1 ml deoxygenated 0.5M Tris-HCl pH 7.7, 10 mM EDTA, 6M guanidine-HCl. Dithiothreitol was added to a final concentration of 5–10 mM, and the reduction was allowed to proceed at 37° C. for 30 min. A 0.5-fold molar excess of [$^{14}C$]iodoacetamide (24 mCi/mmole) over total sulfhydryl groups was added, and the incubation continued at 37° C. for 60 min. in the dark. The alkylation was terminated by addition of a large excess of dithiothreitol over iodoacetamide, and the alkylated bFGF was purified by reverse phase-high performance liquid chromatography.

Performic acid oxidation of cysteine converts cysteine to cysteic acid, and the cysteic acid content of the protein is measurable by amino acid analysis. Performic acid was generated by incubating 9 ml distilled formic acid with 1 ml 30% $H_2O_2$ at room temperature in a tightly capped tube for 1 hour. 0.25 ml of this solution was employed to dissolve the dried bFGF (5–15 nmoles), and the oxidation was permitted to continue at 0° C. for 2.5 hours. Four lyophilizations from distilled water were employed to remove reaction by-products.

Basic FGFs (with cysteines modified by each method described above) were proteolytically and chemically digested to obtain fragments for further analysis, including sequence analysis. Prior to any digestion, the bFGF was dried in a polypropylene microfuge tube in a Speed Vac vacuum centrifuge from volatile RP-HPLC solvents.

In order to obtain multiple, overlapping bFGF fragments, three types of proteolytic digestions of bFGFs, with cysteines modified by each method described above, were performed as follows. The dried bFGF (1–5 nmoles) was dissolved in 0.01 ml 0.5M Tris-HCl pH 7.7, 10 mM EDTA, 6M guanidine-HCl and then diluted to 1 ml with 1% $NH_4HCO_3$. Submaxillaris protease or chymotrypsin was added in a 1/50 (w/w) ratio while digestions with *Staphylococcus aureus* V8 employed a 1:35 (mol:mol) ratio of enzyme to substrate. Submaxillaris protease cleaves at the C-terminus of arginine; *Staphylococcus aureus* V8 cleaves at the C-terminus of glutamic acid; and chymotrypsin cleaves at the C-terminus of several amino acid residues having bulky aromatic or hydrophobic groups. Incubations were allowed to proceed overnight at 37° C.

Digestion with cyanogen bromide, which cleaves proteins at the C-terminus of Met, were performed on bFGFs, with cysteines modified by each method described above, as follows. The dried, alkylated bFGF (5–6 nmoles) was dissolved with 0.05 ml 70% formic acid and reduced in a solution of 2.9M N-methylmercaptoacetamide in 7% formic acid (R. Houghten et al. *Methods in Enzymol.* (eds. Hirs., C. & Timasheff, S.) 91: Academic Press, New York, pp. 549–559 (1983)) for 24 hours at 37° C. The alkylated, reduced bFGF was purified by RP-HPLC, dried in a Speed Vac vacuum centrifuge and redissolved in 0.1 ml deoxygenated 70% formic acid. A 100-fold excess of cyanogen bromide was added and the incubation continued at room temperature in the dark overnight.

Reverse phase-high performance liquid chromatography purifications of modified bFGFs and their digestion fragments were accomplished using a Brownlee RP-300 reverse phase column (0.46×25 cm) and a 0.1% TFA/acetonitrile or a 0.1% heptafluorobutyric acid (HFBA)/acetonitrile solvent system (Esch et al. (1983), supra)

Amino acid analyses and gas phase micro-sequencing of intact bFGF and its digestion fragments were carried out by methods previously described (P. Bohlen et al., *Anal. Biochem.* 126: 144–152 (1982); F. S. Esch, *Anal. Biochem.* 136:39–47 (1984)). PhNCS-($^{14}C$)-carboxyamidomethylcysteine was identified during sequence analysis by liquid scintillation counting of the residues from the sequencer. The identification of cysteic acid in a given cycle was accomplished by comparison of the amino acid composition of the peptide and the remainder of its sequence as determined by Edman degradation. Carboxypeptidase Y was obtained from Pierce and utilized according to the manufacturer's recommendations. Carboxyl terminal analysis via tritium incorporation was accomplished as previously described (H. Matsuo et al. *Protein Sequence Determination* (ed., Needleman, S. B.) Springer-Verlag, New York, pp. 104–113 (1979)).

The highly efficient purification procedure, described above, permitted the rapid isolation of large quantities (about 30 to 60 nmoles per week) of highly purified basic FGF from bovine pituitaries. This source aided in the structural characterization effort. The heparin-Sepharose affinity chromatography purification step resulted in a several thousand-fold purification of two biologically active and basic FGF-immunoreactive mitogens, eluting at approximately 1.4M and 1.95M NaCl. A single step of RP-HPLC effected peptide homogeneity in each case. $NaDodSO_4$ PAGE yielded identical molecular weight estimates for both species, and gas phase micro-sequencing showed that both possessed identical amino terminal amino acid sequences through at least the amino-terminal 24 residues of each polypeptide. Pituitary extracts yielded approximately 15 times more of the mitogen eluting at 1.4M NaCl than of the later eluting species, and hence, the former was selected for further structural characterization.

$NaDodSO_4$ PAGE suggested a molecular weight of 16,250±1000 for bovine pituitary basic FGF. Table II below shows the amino acid compositions obtained for the cationic mitogen from bovine brain and hypothalamus by R. R. Lobb et al., *Biochem.* 23:6295–6299 (1984) as well as the compositional data obtained for basic FGF from bovine pituitary, all data being normalized for a 146 amino acid structure. The similarity of the compositions suggests that these structures are closely related, if not identical. In fact, basic FGF from bovine brain has been isolated, and it has been determined that its amino terminal sequence is identical to that of the pituitary-derived molecule.

TABLE II

AMINO ACID COMPOSITIONS OF BASIC FGF FROM DIFFERENT BOVINE TISSUES

| Amino Acid | Brain[a] | Hypothalamus[a] | Pituitary | Basic FGF[b] (1–146) |
|---|---|---|---|---|
| Asx | 13.7 | 13.0 | 12.4 ± 0.4 | 12 |
| Thr | 5.1 | 4.9 | 3.9 ± 0.3 | 4 |
| Ser | 10.0 | 10.0 | 9.4 ± 0.6 | 10 |
| Glx | 13.2 | 14.2 | 14.1 ± 0.4[c] | 12 |
| Pro | 11.6 | 11.3 | 9.4 ± 0.6 | 10 |
| Gly | 17.3 | 18.2 | 16.6 ± 0.6[c] | 15 |
| Ala | 9.1 | 9.0 | 9.5 ± 0.4 | 9 |
| Cys | n.d. | n.d. | 4.3 ± 0.2[d] | 4 |
| Val | 5.8 | 5.7 | 5.9 ± 0.7 | 7 |
| Met | 2.4 | 2.4 | 1.6 ± 0.4 | 2 |
| Ile | 3.2 | 3.1 | 3.4 ± 0.5 | 4 |
| Leu | 12.6 | 12.9 | 13.4 ± 0.4 | 13 |
| Tyr | 6.5 | 6.2 | 6.8 ± 0.4 | 7 |
| Phe | 7.9 | 7.6 | 7.5 ± 0.2 | 8 |
| His | 3.2 | 3.2 | 2.4 ± 0.6 | 3 |
| Lys | 13.7 | 13.5 | 13.9 ± 0.7 | 14 |
| Arg | 10.8 | 10.4 | 11.6 ± 0.3 | 11 |
| Trp | n.d. | n.d. | 0.4 ± 0.2 | 1 |

[a]Data from Lobb, et al., supra, normalized for 146 amino acids.
[b]Amino acid composition of basic FGF deduced from sequence analysis.
[c]Discrepancy between amino acid and sequence analysis data greater than that expected from statistical analysis.
[d]Cysteine was determined as cysteic acid after RP-HPLC purification of performic acid oxidized basic FGF.

EXAMPLE 2

Using conventional methods, described in CSH, supra., a synthetic mammalian bFGF gene is constructed having the following formula:

```
5'  AATTCATGCCAGCCCTACCAGAAGATGGGGGGTCCGGGGCCTTCCCACCAGGG
3'       GTACGGTCGGGATGGTCTTCTACCCCCCAGGCCCCGGAAGGGTGGTCCC
         CACTTCAAAGATCCAAAACGACTATATTGTAAAAACGGGGGGTTC
         GTGAAGTTTCTAGGTTTTGCTGATATAACATTTTTGCCCCCCAAG
         TTCCTACGAATCCACCCAGATGGGCGAGTAGATGGGGTACGAGAA
         AAGGATGCTTAGGTGGGTCTACCCGCTCATCTACCCCATGCTCTT
         AAATCCGATCCACACATCAAACTACAACTACAAGCCGAAGAACGA
         TTTAGGCTAGGTGTGTAGTTTGATGTTGATGTTCGGCTTCTTGCT
         GGGGTAGTATCCATCAAAGGGGTATGTGCCAACCGATATCTAGCC
         CCCCATCATAGGTAGTTTCCCCATACACGGTTGGCTATAGATCGG
         ATGAAAGAAGATGGGCGACTACTAGCCTCCAAATGTGTAACCGAT
         TACTTTCTTCTACCCGCTGATGATCGGAGGTTTACACATTGGCTA
         GAATGTTTCTTCTTCGAACGACTAGAATCCAACAACTATAACACC
         CTTACAAAGAAGAAGCTTGCTGATCTTAGGTTGTTGATATTGTGG
         TATCGATCCCGAAAATATTCCTCCTGGTATGTAGCCCTAAAACGA
         ATAGCTAGGGCTTTTATAAGGAGGACCATACATCGGGATTTTGCT
         ACCGGGCAATATAAACTAGGGCCAAAAACCGGGCCAGGGCAAAAA
         TGGCCCGTTATATTTGATCCCGGTTTTTGGCCCGGTCCCGTTTTT
         GCCATCCTATTCCTACCAATGTCCGCCAAATCCTAAG      3'
         CGGTAGGATAAGGATGGTTACAGGCGGTTTAGGATTCAGCT 5'
```

Synthesis of a bFGF-encoding DNA chain is accomplished by synthesizing oligonucleotides on an Applied B10 Systems automatic synthesizer with overlapping complementary sequences.

The overlapping oligonucleotides are fused to form a double-stranded DNA chain, gaps being filled in with DNA polymerase and with T4 ligase. Immediately 5' of the FGF-encoding sequence in the sense strand is provided an ATG start signal, which results in an extraneous methionine being added to the N-terminus of the expressed polypeptide. Immediately 3' of the bFGF-encoding sequence is a stop signal. At the 5' end is a Eco RI overhang and at the 3' end is a Sal I overhang, whereby the synthetic DNA strand is directly insertable in the Eco RI and Sal I site of the plasmid pUC8, described by Vieira et al. Gene 14: 259–268 (1982). The DNA strand is annealed into the pUC8 plasmid where it is under the control of the beta galactosidase promoter with the ATG start signal and the Shine Delgarno sequence retained in their natural orientation and association with the promoter.

The recombinant vector, designated bFGF, is transformed into the DH-1 strain of E. coli by the calcium chloride procedure, CSH, supra.

The transformed E. coli is cultured in L broth, and ampicillan-resistant strains are selected. Because the DNA chain was inserted into the plasmid in an orientation which could be expected to lead to expression of protein product of the DNA chain, the ampicillan-resistant colonies are screened for reactivity with antiserum raised against bFGF extracted from the pituitary. These colonies are screened by the immunological method of Healfman et al., Proc. Natl. Acad. Sci. USA 80: 31–35 (1983), and colonies reacting positively with bFGF antibody are further characterized. The cells are separated from their culture media are lysed, and their supernatant obtained. Supernatant from transformed cells is determined by RIA to be reactive with antibody raised against bFGF.

100 ml. of cell supernatant is obtained, and bFGF is purified therefrom using heparin-Sepharose as described above. Approximately 0.01 mg of bFGF, purified to upwards of 98% by weight of total protein, is produced.

The biological activity of the synthetic bFGF, which contains the extraneous N-terminal methionine residue, is tested for biological activity by the ability of the synthetic bFGF to stimulate the proliferation of adult bovine aortic arch endothelial cells in culture, as described in J. Cell Biol. 97: 1677–1685 (1983). Briefly, cells (at passage 3–10) are seeded at a density of $2\times10^3$ cells/dish on plastic tissue culture dishes and exposed to Dulbecco's modified Eagle's medium (DMEM) supplemented with 10% calf serum. Test samples, at a dilution ranging from $10^{-1}$ to $10^{-3}$ are added on day 0 and day 2 to the dishes. On day 4, triplicate dishes are trypsinized and counted in a Coulter counter. Background levels are ordinarily $10^5$ cells/dish, while those exposed to optimal concentrations of the growth factor can contain as much as 5 to $8\times10^5$ cells. For a potency assay, a log response curve was established. For this purpose, 10 microliter-aliquots of a dilution (ranging from $10^{-1}$ to $10^{-5}$) of the original solution made in 0.5% BSA/DMEM were added in triplicate.

The biological (mitogenic) activity of synthetic bFGF is substantially identical to natural purified bFGF from bovine pituitary cells.

The superfluous N-terminal residue is removable by partial chemical digestion with cyanogen bromide or phenyl isothiocyanate followed by treatment with a strong anhydrous acid, such as trifluoroacetic acid. However, this process attacks internal Met residues, and while providing some bFGF having the natural protein structure, substantially reduces the total amount of biologically active protein.

EXAMPLE 3

Plasmid bFGF, amplified in one of the bFGF-producing E. coli clones of Example 2, is isolated and cleaved with Eco RI and Sal I. This digested plasmid is electrophoresed on an agarose gel allowing for the separation and recovery of the amplified bFGF insert. The insert is inserted into the plasmic pYEp, a shuttle vector which can be used to transform both E. coli and Saccharomyces cerevisiae yeast. Insertion of the synthetic DNA chain at this point assures that the DNA sequence is under the control of a promoter, in proper reading frame from an ATG signal and properly spaced relative to a cap site. The shuttle vector is used to transform URA3, a strain of S. cerevisiae from which the oratate monophosphate decarboxylase gene is deleted.

The transformed yeast is grown in medium to attain log growth. The yeast is separated from its culture medium, and cell lysates are prepared. Pooled cell lysates are determined by RIA to be reactive with antibody raised against bFGF, demonstrating that a peptide containing bFGF peptide segments is expressed within the yeast cells.

EXAMPLE 4

This example describes the cloning and expression of cDNA and genomic clones encoding mammalian basic FGFs, all of which is based on the elucidation of the amino acid sequence of bovine basic FGF. The description is taken from three reports: Abraham, J. et al., *Science* 233: 545–548 (1986); Abraham J. et al. *EMBO* 5:2523–2528 (1986); and PCT application US86/01879 (published as WO 87/01728 on Mar. 26, 1987), all three of which are incorporated herein by reference.

An oligonucleotide probe for bovine basic FGF was designed taking into account the amino acid sequence homology between basic and acid bovine FGFs. In particular, the homology between amino acids 18 to 31 of basic FGF and amino acids 9 to 22 of acidic FGF were used to design a 40-base oligonucleotide probe. Where the two amino acid sequences are identical, the probe contains the same codon choice as that found in the acidic FGF genomic fragment; at positions where the sequences differ, the probe incorporates the minimum possible number of nucleotide changes needed to allow the amino acid change.

It was expected that this oligonucleotide would hybridize to both acidic and basic FGF sequences, but that at conditions of higher stringency it would be specific for basic FGF. The appropriate hybridization conditions to obtain this specificity were established through Southern blots of bovine genomic DNA that were washed at increasing stringencies. At both 50° and 55° C. wash temperatures, a number of hybridizing fragments were detected, including two known acidic FGFs. At a 65° C. wash temperature, these acidic FGF fragments were no longer detectable, and the remaining 3.5 kilobase (kb) Pst I and 10.0-kb Eco RI fragments presumably corresponded to basic FGF.

A bovine pituitary complementary DNA (cDNA) library of approximately $10^6$ independent recombinants was made in bacteriophage λgt10 and screened with the probe (labelled with $^{32}p$) using a 65° C. wash temperature. A single hybridizing recombinant was isolated and shown by DNA sequence analysis to be a cDNA clone of 2122 bp encoding bovine basic FGF.

The nucleotide sequence corresponding to the published 146 amino acid sequence of bovine basic FGF can be identified in the clone. Basic FGF does not appear to be synthesized initially as a precursor with an extended carboxyl terminus, because a termination codon directly follows the codon for amino acid 146. The 3'-untranslated region has 1554 nucleotides and contains neither a polyadenylation recognition signal nor a polyadenylate tail, suggesting that the cDNA clone is incomplete at the 3' end.

The nucleotide sequence of clone has an open reading frame extending upstream from the codon for the amino-terminal proline of mature basic FGF, and continuing to the end of the clone. Thus, basic FGF appears to be synthesized initially as a precursor with a long amino-terminal extension, and the initiator methionine may not be encoded by the clone.

A λgt10 cDNA library prepared from human kidney mRNA was probed using a 1.4 kb Eco RI bovine basic FGF subfragment. Prehybridization/hybridization buffer contained 40% formamide, 5 mM Na phosphate, pH 6.5, 5×Denhardt's, 5×SSC, and 50 μg/ml herring sperm DNA; hybridization buffer also included 10% dextran sulfate and $10^4$–$10^5$ cpm/ml probe. Three clones were isolated.

Thereafter, additional genomic (lambda Charon 4A and 28) and cDNA (human fetal liver) libraries were screened using the same 1.4 kb bovine bFGF-encoding fragment under precisely the same hybridization conditions. Four additional clones were obtained, which between them encode a 146 amino acid protein. Nine upstream codons translate into a sequence having complete homology with the translated upstream codons in bovine basic FGF clone, although there is a silent nucleotide substitution in codon –8.

The two amino acid differences between bovine bFGF and human bFGF are the result of a single nucleotide difference in each case; therefore bovine cDNA may conveniently be modified by site directed mutagenesis as described below to encode the human protein, and, indeed, standard site-specific mutagenesis techniques were used to alter these codons. The bovine basic FGF cDNA was digested with Eco RI and the 1.4 kb region spanning the bFGF protein-encoding portion was ligated into the Eco RI site of M13mp8. The in vitro mutagenesis was carried out in the presence of three oligonucleotides: the "universal" primer, a 17-mer; the mutagenic 16-mer 5'-GAAATACAC-CAGTTGG-3'; which alters the coding sequence at codon 112, and the mutagenic 17-mer 5'-ACTTGGATCCAAAA-CAG-3', which alters the sequence at codon 128. The mutagenized phage was also subjected to a second round of in vitro primer-directed mutagenesis to create a Hind III site 34 bp downstream from the translation termination codon using the mutagenic 25-mer, 5'-TTTTACATGAAGCTT-TATATTTCAG-3'. The resultant mutated DNA was sequenced by dideoxy sequencing to confirm that the desired mutagenesis had occurred, and the approximately 630 bp fragment spanning the FGF coding region was excised with Hind III and ligated into pUC13. Of course, modified forms of the coding sequence of any of the three known N-terminal modifications of basic FGF may also be prepared by using standard synthesis techniques.

EXAMPLE 5

This example describes experiments demonstrating microbial expression of various mammalian FGF polypeptides, the sequences of which are primarily based on the deduced bovine basic FGF sequence.

Chemical gene synthesis has been shown to be an efficient alternative to the molecular cloning of cDNAs for proteins for which the complete amino acid sequences are known. A 456 bp gene for bovine basic FGF (1–146) was chemically synthesized. Codon usage was primarily based on the codon bias for bovine pituitary growth hormone (bGH). Also, a unique restriction enzyme target for Nar I was incorporated close to the 5'-end of the bovine basic FGF gene. This allowed the facile transfer of the gene into various expression systems using synthetic adapters. Since mature bovine and human basic FGFs differ in only two amino acids, (i.e., human basic FGF has a Thr at position 112 and a Ser at position 128), only seven new oligonucleotides of between 18 and 43 bases were needed for the synthetic human basic FGF gene (not including the precursor). These were ligated, along with the appropriate bovine oligonucleotide sequences, to give the human basic FGF gene.

A. DNA Synthesis and Gene Assembly.

Oligoucleotides were synthesized by the phosphoramidite method using Applied Biosystems 380A synthesizers. β-Cyanoethoxyphosphoramidite intermediates (American Bionetics, Hayward, Calif.), and o-nitrophenyltetrazole activating agent (Turbo activator, American Bionetics) were used for the synthesis of oligonucleotides varying in length between 18 and 45 bases. Typically, a full gene comprised of approximately 22 such oligonucleotides with maximum overlap between complementary oligonucleotides. Purification of oligonucleotides has been described in Urdea, M. et al., *P.N.A.S. U.S.A.* 80:7461 (1983). Each synthetic fragment was preparatively phosphorylated, the mixed oligonucleotides heated to 90° and the mixture was allowed to cool to 25° C. over 3h in a buffer containing 20 mM Tris-HCl, pH 8.0, 10 mM $MgCl_2$, and 10 mM dithiothreitol. After annealing, the mixture was made 3 mM in ATP. Ligation for 15 min at 25° C. with T4 DNA ligase (5 µL, New England Biolabs, $4\times10^5$ U/ml) was followed by ethanol precipitation and digestion with Xba I and Jal I. Each synthetic bovine gene was purified by polyacrylamide gel electrophoresis on 7% acrylamide, electroeluted and cloned into Xba-I/Sal I digested pHG100. The corresponding human genes were similarly purified and cloned into Nco I/Sal I digested pBS100 (Barr, P. et al., *Vaccine* 5:90 (1987), which is incorporated herein by reference). These plasmids were digested with Bam H1 to release expression "cassettes," which were cloned into the Bam H1 digested and alkaline phosphatase treated yeast plasmid pAB24. Gene sequences and subsequent expression vector junction sequences were verified by M13 dideoxy sequencing. For the several particularly G-C rich regions of the basic FGF genes, the dGTP analog, 7-deaza-dGTP, was used to resolve compressed areas of sequence information.

B. Plasmids.

The plasmid pHG100 is derived from pBR322 and is analogous to pAB114 (Brake, A. et al., *P.N.A.S. U.S.A.* 81:4642 (1984), which is incorporated herein by reference). Each plasmid contains the *S. cerevisiae* α-factor structural gene in pAB114, and a synthetic human interleukin-2 (hIL-2) gene in pHG100. In addition, pHG100 was modified by introduction of silent mutations encoding a unique Xba I cloning site immediately 5' to the mature hIL-2 coding sequence. For expression studies, these α-factor leader-synthetic gene constructs were fused to the ADH-2/GAPDH promoter described previously, to give vectors designated pA/Gα-factor bFGFs. pBS100 contains a Bam H1 expression "cassette" consisting of the hybrid ADH-2/GAPDH promoter and the GAPDH transcriptional terminator. These control elements flank a region of the human immunodeficiency virus (HIV) env gene. Cloning sites for these constructions are Nco I, which encodes the methionine initiation codon and Sal I which is situated downstream of termination codons of the gene to be expressed. The yeast plasmid pAB24 is described in Barr, P. et al., *Biotechnology* 5:486 (1987). This plasmid contains selectable markers for growth in either uracil or leucine deficient media. The use of ptac5SOD for expression of hSOD fusion proteins in *E. coli* is described in Steimer, K. et al. *J. Virol.* 58:9 (1986), which is incorporated herein by reference.

C. Strains. For transformation and expression in *E. coli*, the common strain D1210 was used (Maniatis, T. et al., *Molecular Cloning, a Laboratory Manual*, Cold Spring Harbor, N.Y. (1982), which is incorporated herein by reference). The yeast strains used are as follows: *S. cerevisiae* AB110 (Matα, leu 2-3,112ura3-52, pep4-3, his4-580, [cir°]); 2150-2-3 (Matα leu2, adel, [cir°]); BJ2168 (Mata, leu2, trp-1, ura3-52, prB1-1122, pep4-3, prCl-407, [cir°]. Yeast transformations were performed as described in Hinnen, A. et al., *P.N.A.S. U.S.A.* 75:1919 (1978).

D. Purification of FGFs from recombinant bacterial and yeast cultures.

Each FGF was purified by heparin sepharose chromatography. Briefly, extracts from lysed bacteria or yeast were loaded directly onto columns of heparin sepharose (Pharmacia) in Tris buffer (10 mM, pH 7.0, 1 MM EDTA) with 1.0M NaCl (for basic FGFs). For elution from heparin sepharose, NaCl gradients up to 3.0M (basic FGFs) were used. For final purification of *E. coli* derived bovine basic FGF, a subsequent gel filtration on Ultrogel AcA54 (LKB) in 20 mM Tris, pH7.5, O.1 mM EDTA, 0.3M NaCl was also included.

The N-terminally acetylated and unblocked forms of human basic FGF were separated by reverse phase HPLC on a Vydac C-4 column (0.46×25 cm, the Separations Group). The column was equilibrated with 0.1% trifluoroacetic acid (TFA), and human basic FGFs were eluted using a gradient of 32 to 34% acetonitrile. N-terminal sequence analysis of all purified FGFs was performed using an Applied Biosystems 470A gas phase sequenator with on-line HPLC analysis of PTH-amino acids.

E. Peptide Mapping.

The two forms of human basic FGF resolved by HPLC were reduced with DTT and treated with vinylpyridine to block the cysteine residues. After digestion with *Staphylococcus aureus* V8 protease, the peptides were separated by HPLC on a Vydac C-18 column (0.46×25 cm) in 0.1% TFA, using a 50 minute gradient of 10 to 40% acetonitrile. Each peak was collected and subsequently identified by amino acid composition analysis.

F. Mass Spectrometry.

Assignments of protonated molecular ions of N-terminal peptides was established using a Kratos MS50S double-focussing instrument equipped with a high-field magnet, LSIMS source and a post-accelerator detector (10 KeV) in the positive ion mode. Samples were applied to the probes and dried in vacuo. A matrix of thioglycerol:glycerol (1:1) containing hydrochloric acid was applied prior to insertion into the source. Spectra were scanned from m/e 3000-300.

G. Mitogen Assay for FGF.

The mitogenic activity of the various FGFs was assayed using density arrested human foreskin fibroblasts (HFF). Cells were plated (1×104)/well) in 96 will microtiter plates in Dulbecco's Modified Eagles Medium (DMEM) with 5% fetal bovine serum (Hyclone, Ogden, Utah). After 5 days, dilutions of various FGF preparations were added in 10 µl of serum-free DMEM. 18 hours later, $^3$H-Thymidine (1 µci/well; Amersham, 25 Ci/mmol, 103 mci/mg), was added and the plates returned to the incubator. Plates were incubated for 24 h and then the cultures washed with Phosphate buffered saline (PBS). Trichloroacetic acid (5%) was added to the wells for 15 minutes and then the wells received methanol for 15 minutes. The plates were then flooded with 100% methanol and air dried. The contents of each well was then solubilized in 50 µl 0.3N NaOH and transferred to vials containing scintillation fluid for counting. Each dilution of FGF sample was assayed in triplicate. One unit of activity is the amount of FGF required to stimulate half-maximal $^3$H-Thymidine incorporation. The specific activity of various preparations was determined by dividing the reciprocal of the dilution yielding half-maximal incorporation by the protein concentration (nanograms).

H. Bovine Basic FGF Gene Expression.

The synthetic gene for bovine basic FGF (1-146) was expressed in *E. coli* using a two cistron message driven by the Tac-1 promoter. The highly expressed human superoxide dismutase (hSOD) gene (see, EPA 84111416.8, which is incorporated herein by reference) was used to provide the first cistron of the message. This gene was followed by a new ribosome binding site, a stop codon, and an initiation codon for the bovine FGF gene. IPTG induction of *E. coli* strain D1210 cells transformed with these plasmids allowed the moderate level expression of bovine FGFs.

This gene was also expressed as a fusion with the yeast α-factor mating pheromone leader sequence. Synthetic adapters were used to fuse each gene to sequences encoding this secretion and processing signal. This hybrid gene was flanked by the glucose regulatable alcohol dehydrogenase-2 (ADH-2)/glyceraldehyde-3-phosphate dehydrogenase (GAPDH) hybrid promoter and the α-factor transcriptional terminator. Secreted FGF was detected in the yeast supernatants by SDS-PAGE analysis of precipitated protein from TCA treated media and by bioassay.

In order to accurately define N-terminal amino acid structures and specific activities of each recombinant bovine FGF, each protein was purified from both *E. coli* cells and *S. cerevisiae* supernatants. This was accomplished utilizing heparin-sepharose chromatography as described previously. Using this procedure, substantially homogeneous bovine basic FGF samples (typically greater than 98% purity) were obtained. N-terminal amino acid sequence analysis was performed on each of these purified samples, and the results are shown in Table 3 (for human basic FGF precursor, each alanine residue immediately subsequent to the initiation codon derived methionine is referred to as amino acid 1).

directly to the ADH-2/GAPDH hybrid promoter.

An expression cassette vector was constructed by cloning a synthetic gene encoding the N-terminal extended form of human basic FGF into a yeast expression vector as done for the bovine FGF. The synthetic gene had the following formula:

```
CATGGCCGCCGGGAGCATCACCACGCTGCCAGCCCTGCCGGAGGACGGGGG
CAGCGGCGCCTTCCCCCCAGGCCATTTCAAGGACCCAAAGAGACTGTACTG
TAAGAACGGCGGGTTCTTCCTGAGAATCCATCCCGACGGCAGGGTCGATGG
CGTGAGAGAGAAGAGCGACCCTCATATCAAGCTTCAGCTGCAGGCCGAGGA
GAGGGGCGTGGTCTCCATCAAGGGCGTCTGTGCCAACAGGTACCTGGCCAT
GAAGGAGGACGGCAGGCTGCTGGCCTCCAAGTGTGTCACCGACGAGTGTTT
CTTCTTCGAGAGGCTGGAGTCCAACAACTACAACACCTACCGGTCAAGGAA
ATACACCAGCTGGTACGTCGCCCTGAAGAGGACCGGCCAGTACAAGCTGGG
ATCCAAAACAGGACCTGGGCAGAAGGCCATCCTGTTCCTGCCCATGTCCGC
CAAGTCCTAATAGTCGAC
```

Plasmids containing these sequences were used to transform yeast under conditions of leucine selection. Induction of FGF gene expression occurred concomitantly with depletion of glucose in the yeast media during culture growth. Since FGFs are observed extracellularly in vivo, supernatants of these cultures were examined for exported FGF. In each case, FGF polypeptides were found only in the soluble fraction of the disrupted yeast cells. Insoluble yeast debris and supernatants contained very little FGF (less than 5% of total). These soluble human basic FGF polypeptides were readily purified on heparin-sepharose. Each purified hFGF was analyzed by N-terminal sequence analysis. As predicted

TABLE 3

| Construction (See FIG. 1) | Bacterial Yeast Strain | NH$_2$-terminal sequences | | Specific activity (U/mg × 10$^{-5}$) |
|---|---|---|---|---|
| A bovine basic FGF | *E. coli* D1210 | 1 Pro-Ala-Leu- Ala-Leu | (54%) (46%) | 8.9 |
| B bovine basic FGF | *S. cerevisiae* AB110 | −1  1 Arg-Pro-Ala-Leu- | (74%) | 8.0 |
| C human basic FGF | *S. cerevisiae* BJ2168 | Acetyl-Ala-Ala- Ala-Ala- | (50%) (50%) | 9.3 |

The *E. coli* derived bovine basic FGF (1-146), although quantitatively processed with regard to methionine removal, was further degraded to a heterogeneous mixture of bovine basic FGF species. Similarly, bovine FGF was shown to have heterogeneous N-termini when secreted from yeast. Secreted bovine basic FGF was found to contain a major species which included the processing site-derived arginine in addition to authentic bovine basic FGF (1-146).

I. Human basic FGF Precursor Expression.

Corresponding human FGFs as precursor forms were expressed using an intracellular yeast expression system. Using initiation codons predicted from protein analysis and DNA sequence data for human basic FGF (Abraham, J. et al., *EMBO* 5:2523–2528 (1986)) synthetic precursor genes (i.e., encoding the following additional N-terminus amino acids: (Met)-Ala-Ala-Gly-Ser-Ile-Thr-Thr-Leu) were fused from previous studies with hSOD expressed in yeast, the haFGF precursor was found to be quantitatively blocked at the N-terminus. Mass spectral analysis of tryptic fragments of this polypeptide demonstrated that the blocking group was the acetyl moiety. This data, together with amino acid sequence analysis, also showed that endogenous yeast methionyl aminopeptidase was able to efficiently cleave the initiation codon-derived methionine residue prior to acetylation.

Purification and analysis of the expressed human basic FGF precursors showed that the N-terminal methionine was quantitatively removed; however, N-termini peptide mapping, quantitative amino acid sequence analysis and mass spectroscopy showed that human basic FGF was only partially modified by acetylation. This situation in some way mimics the results of isolation of basic FGFs from mammalian tissue in that human basic FGF from human benign prostatic hyperplastic tissue was found to contain the unblocked N-terminus Ala-Ala-Gly- etc. Material isolated and purified from a human hepatoma was, however, found to be blocked, as was a similar higher molecular weight bovine basic FGF from bovine pituitary.

The cDNA clones encoding basic FGF are most conveniently used to produce the recombinant proteins in a variety of hosts. However, expression in mammalian systems is favored as the host is capable of post translational processing analogous to that experienced by the natively produced protein, and either cDNa or genomic sequences may be used, as the host is also capable of processing introns.

Thus, a full-length cDNA or genomic FGF encoding clone is prepared for insertion into a host vector. To construct the vectors, the cloned FGF-encoding insert is excised with Eco RI (by partial digestion if the insert itself contains Eco RI sites) or other appropriate enzyme, provided with Eco RI or other appropriate linkers if necessary, and then inserted into an appropriate host vector in accordance with the art.

The invention provides novel bFGF polypeptide compositions and should make this important material available for biological and therapeutic use. The production of bFGF can be carried out in both prokaryotic and eukaryotic cell lines. While bFGF synthesis is easily demonstrated using either bacteria or yeast cell lines, the synthetic genes should be insertable for expression in cells of higher animals, such as mammalian tumor cells. Such mammalian cells may be grown, for example, as peritoneal tumors in host animals, and bFGF harvested from the peritoneal fluid.

Although the above examples demonstrate that bFGF can be synthesized through recombinant DNA techniques, the examples do not purport to have maximized bFGF production. It is expected that subsequent selection of more efficient cloning vectors and host cell lines will increase the yield of bFGFs. Known gene amplification techniques for both eukaryotic and prokaryotic cells may be used to increase production of bFGF. Secretion of the gene-encoded polypeptide from the host cell line into the culture medium is also considered to be an important factor in obtaining synthetic bFGF in large quantities.

Various bFGFs may also be synthesized using either classical synthesis and/or solid-phase synthesis to produce peptide segments of reasonable length. Such segments can then be appropriately linked to one another to create the desired 146-residue, 154 or 155-residue, or other sized molecules or modifications thereof.

Brain and pituitary bFGF preparations, as reported earlier, are mitogenic for a wide variety of normal diploid cultured cells derived from tissue originating from the primary or secondary mesenchyme, as well as from neuroectoderm. These include rabbit chondrocytes, bovine granulosa and adrenal cortex cells, bovine corneal endothelial cells, capillary endothelial cells derived from bovine adrenal cortex and human umbilical endothelial cells. (See, generally, Baird, A. et al., *Recent Progress in Hormone Research* 42:143–205 (1986), which is incorporated herein by reference.) bFGF peptides are useful biological materials for promoting in vitro growth of cultured cell lines, such as cell lines that have been transformed by recombinant DNA techniques to produce other useful polypeptides. They are also particularly useful for enhancing wound healing.

Furthermore, studies have shown that bFGF is capable of nerve regeneration, eliciting an angiogenic response, for example, when implanted in the hamster cheek pouch or in the chick chorioallantoic membrane. Accordingly, substantially pure (e.g., 95 to 99% or more) bFGF peptides have numerous potential therapeutic applications.

Substantially pure bFGF polypeptides can be routinely obtained having significantly higher purity than bFGF polypeptides that are extracted from mammalian tissues, such as bovine pituitaries. Typically, bFGF polypeptides constitute only very minor constituents of normal mammalian tissues and, thus, are present only in very impure form, relative to other native polypeptides also present. As indicated above, recombinant DNA techniques, for example, can be used to generate organisms or cell lines that produce the heterologous polypeptide in significantly higher proportions relative to total protein, in the cellular material and/or their secretions, than the proportions at which native bFGF polypeptides are present in mammalian tissue. Because the starting material from which such synthetic bFGF polypeptides are isolated has a substantially greater concentration of the heterologous polypeptide, purification techniques can fairly simply produce more highly purified bFGF polypeptide fractions. Using isolation techniques such as those described in detail in the above-identified U.S. Ser. Nos. 586,518, 670,160, and particularly 940,524, now U.S. Pat. No. 4,785,079, is possible to routinely obtain bFGF polypeptides which are at least about 98% pure (by weight of total proteins) and which is herein referred to as substantially pure.

Substantially pure synthetic bFGF or the nontoxic salts thereof, combined with a pharmaceutically acceptable carrier (e.g., heparin) to form a pharmaceutical composition, may be administered to mammals, including humans, either intravenously, subcutaneously, intramuscularly or orally. The required dosage will vary with the particular condition being treated, with the severity of the condition and with the duration of desired treatment.

Such peptides are often administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically-acceptable carrier. If desired, bFGF polypeptides may be administered in conjunction with other therapeutic agents, including other mitogens, such as platelet-derived growth factor, epidermal growth factor, insulin-like growth factors, and transforming growth factors.

Although the invention has been described with regard to its preferred embodiments, which constitute the best mode presently known to the inventors, it should be understood that various changes and modifications, as would be obvious to one having the ordinary skill in this art, may be made without departing from the scope of the invention which is set forth in the claims appended hereto.

Particular features of the invention are emphasized in the claims which follow.

What is claimed:

1. An isolated DNA sequence comprising a nucleotide sequence encoding the amino acid sequence of bovine basic fibroblast growth factor (FGF) as follows:

Pro—Ala—Leu—Pro—Glu—Asp—Gly—Gly—Ser—Gly—Ala—
Phe—Pro—Pro—Gly—His—Phe—Lys—Asp—Pro—Lys—Arg—
Leu—Tyr—Cys—Lys—Asn—Gly—Gly—Phe—Phe—Leu—Arg—
Ile—His—Pro—Asp—Gly—Arg—Val—Asp—Gly—Val—Arg—
Glu—Lys—Ser—Asp—Pro—His—Ile—Lys—Leu—Gln—Leu—
Gln—Ala—Glu—Glu—Arg—Gly—Val—Val—Ser—Ile—Lys—
Gly—Val—Cys—Ala—Asn—Arg—Tyr—Leu—Ala—Met—Lys—
Glu—Asp—Gly—Arg—Leu—Leu—Ala—Ser—Lys—Cys—Val—
Thr—Asp—Glu—Cys—Phe—Phe—Phe—Glu—Arg—Leu—Glu—
Ser—Asn—Asn—Tyr—Asn—Thr—Tyr—Arg—Ser—Arg—Lys—
Tyr—Ser—Ser—Trp—Tyr—Val—Ala—Leu—Lys—Arg—Thr—
Gly—Gln—Tyr—Lys—Leu—Gly—Pro—Lys—Thr—Gly—Pro—
Gly—Gln—Lys—Ala—Ile—Leu—Phe—Leu—Pro—Met—Ser—
Ala—Lys—Ser.

2. A DNA sequence according to claim 1 which is double-stranded DNA encoding bovine basic FGF constructed by oligonucleotide synthesis.

3. A DNA sequence according to claim 1 which encodes bovine basic FGF and has the formula as follows:

---

| | |
|---|---|
| 5' | AATTCATGCCAGCCCTACCAGAAGATCCGGGTCCGGCCCCTTCCCACCAGGG |
| 3' | GTACGGTCGGGATGGTCTTCTACCCCCAGGCCCCGGAAGGGTGGTCCC |
| | CACTTCAAAGATCCAAAACGACTATATTGTAAAAACGGGGGTTC |
| | GTGAAGTTTCTAGGTTTTCCTGATATAACATTTTTGCCCCCCAAG |
| | TTCCTACGAATCCACCCAGATGGGCGAGTAGATGGGGTACGAGAA |
| | AAGGATGCTTAGGTGGGTCTACCCGCTCATCTACCCCATGCTCTT |
| | AAATCCGATCCACACATCAAACTACAACTACAAGCCCAAGAACGA |
| | TTTAGGCTAGGTGTGTAGTTTGATGTTGATGTTCGGCTTCTTGCT |
| | GGGGTAGTATCCATCAAAGGGGTATGTGCCAACCGATATCTAGCC |
| | CCCCATCATAGGTAGTTTCCCCATACACGGTTGGCTATAGATCGG |
| | ATGAAAGAAGATGGGCGACTACTAGCCTCCAAATGTGTAACCCAT |
| | TACTTTCTTCTACCCGCTGATGATCGGAGGTTTACACATTGGCTA |
| | GAATGTTTCTTCTTCGAACGACTAGAATCCAACAACTATAACACC |
| | CTTACAAAGAAGAAGCTTGCTGATCTTAGGTTGTTGATATTCTGG |
| | TATCGATCCCGAAAATATTCCTCCTGGTATGTAGCCCTAAAACGA |
| | ATAGCTAGGGCTTTTATAAGGAGGACCATACATCGGGATTTTGCT |
| | ACCGGGCAATATAAACTAGGGCCAAAAACCGGGCCAGGGCAAAAA |
| | TGGCCCGTTATATTTGATCCCGGTTTTTGGCCCGGTCCCGTTTTT |
| | GCCATCCTATTCCTACCAATGTCCGCCAAATCCTAAG 3' |
| | CGGTAGOATAAGGATGGTTACAGGCGGTTTAGGATTCAGCT 5' |

* * * * *

UNITED STATES PATENT AND TRADEMARK OFFICE
CERTIFICATE OF CORRECTION

PATENT NO. : 5,464,774            Page 1 of 2

DATED : November 7, 1995

INVENTOR(S) : BAIRD et al.

It is certified that error appears in the above-identified patent and that said Letters Patent is hereby corrected as shown below:

<u>IN THE CLAIMS</u>: Column 23, Claim 3, the formula should read:

```
5'  AATTCATGCCAGCCCTACCAGAAGATGGGGGGTCCGGGCCTTCCCACCAGGG
3'      GTACGGTCGGGATGGTCTTCTACCCCCCAGGCCCCGGAAGGGTGGTCCC

CACTTCAAAGATCCAAAACGACTATATTGTAAAAACGGGGGGTTC
        GTGAAGTTTCTAGGTTTTGCTGATATAACATTTTTGCCCCCCAAG

TTCCTACGAATCCACCCAGATGGGCGAGTAGATGGGGTACGAGAA
        AAGGATGCTTAGGTGGGTCTACCCGCTCATCTACCCCATGCTCTT

AAATCCGATCCACACATCAAACTACAACTACAAGCCGAAGAACGA
        TTTAGGCTAGGTGTGTAGTTTGATGTTGATGTTCGGCTTCTTGCT

GGGGTAGTATCCATCAAAGGGGTATGTGCCAACCGATATCTAGCC
        CCCCATCATAGGTAGTTTCCCCATACACGGTTGGCTATAGATCGG

ATGAAAGAAGATGGGCGACTACTAGCCTCCAAATGTGTAACCGAT
        TACTTTCTTCTACCCGCTGATGATCGGAGGTTTACACATTGGCTA

GAATGTTTCTTCTTCGAACGACTAGAATCCAACAACTATAACACC
        CTTACAAAGAAGAAGCTTGCTGATCTTAGGTTGTTGATATTGTGG
```

UNITED STATES PATENT AND TRADEMARK OFFICE
CERTIFICATE OF CORRECTION

PATENT NO.   :   5,464,774
DATED        :   November 7, 1995
INVENTOR(S)  :   BAIRD et al.

It is certified that error appears in the above-identified patent and that said Letters Patent is hereby corrected as shown below:

```
TATCGATCCCGAAAATATTCCTCCTGGTATGTAGCCCTAAAACGA
ATAGCTAGGGCTTTTATAAGGAGGACCATACATCGGGATTTTGCT

ACCGGGCAATATAAACTAGGGCCAAAAACCGGGCCAGGGCAAAAA
TGGCCCGTTATATTTGATCCCGGTTTTTGGCCCGGTCCCGTTTTT

GCCATCCTATTCCTACCAATGTCCGCCAAATCCTAAG       3'
CGGTAGGATAAGGATGGTTACAGGCGGTTTAGGATTCAGCT    5'
```

Signed and Sealed this

Thirtieth Day of April, 1996

Attest:

BRUCE LEHMAN

Attesting Officer     Commissioner of Patents and Trademarks